United States Patent [19]
Carroll et al.

[11] Patent Number: 5,916,835
[45] Date of Patent: *Jun. 29, 1999

[54] HETEROGENEOUS CATALYST REGENERATION

[75] Inventors: Kevin M. Carroll, Havertown; Edrick Morales; Yuan-Zhang Han, both of West Chester, all of Pa.

[73] Assignee: Arco Chemical Technology, L.P., Greenville, Del.

[*] Notice: This patent issued on a continued prosecution application filed under 37 CFR 1.53(d), and is subject to the twenty year patent term provisions of 35 U.S.C. 154(a)(2).

[21] Appl. No.: 08/770,821

[22] Filed: Dec. 20, 1996

[51] Int. Cl.$^6$ .............................. B01J 20/34; B01J 38/50; B01J 38/52; B01J 38/56
[52] U.S. Cl. ................................ 502/29; 502/31; 502/33
[58] Field of Search .................. 502/29, 30, 31, 502/33; 549/529

[56] References Cited

U.S. PATENT DOCUMENTS

| | | | |
|---|---|---|---|
| 3,923,843 | 12/1975 | Wulff | 260/348.5 L |
| 4,021,454 | 5/1977 | Wulff et al. | 260/348.5 L |
| 4,367,342 | 1/1983 | Wulff et al. | 549/529 |
| 4,876,372 | 10/1989 | Nakanishi et al. | 549/529 |
| 5,011,953 | 4/1991 | Nakanishi et al. | 549/529 |

FOREIGN PATENT DOCUMENTS

| | | |
|---|---|---|
| 0129814 | 6/1984 | European Pat. Off. . |
| 0345856 | 12/1989 | European Pat. Off. . |
| 0 734 764 | 2/1996 | European Pat. Off. ......... B01J 21/06 |
| 0734764 | 3/1996 | European Pat. Off. . |
| 9609117 | 3/1996 | WIPO . |

OTHER PUBLICATIONS

Yen, Propylene Oxide & Ethyl Oxide, Report No. 2C, Apr. 1977, Process E Con. Program (Stanford Research Int), p. 223.

Wang, Propylene Oxide Report No. 2E, Aug. 1994, Process Economics Program (SRI International ) pp. 6–28.

Yen, Propylene Oxide & Ethylene Oxide, Report No. 2C, Apr. 1977, Process Economics Program (Stanford Research Inst.) p. 221.

Cativiela et al., *J. Molecular Catalysis A: Chemical* 112, pp. 259–267 (1996) No Month.

*Primary Examiner*—Michael Lewis
*Assistant Examiner*—Alexander G. Ghyka
*Attorney, Agent, or Firm*—Stephen D. Harper

[57] ABSTRACT

The catalytic activity of a titanium-containing heterogeneous catalyst such as titania-on-silica which has been used to catalyze olefin epoxidation is effectively restored by washing the catalyst with water, alcohol, ether, nitrile, ester, aromatic hydrocarbon, or ketone.

26 Claims, No Drawings

HETEROGENEOUS CATALYST REGENERATION

FIELD OF THE INVENTION

This invention relates to a method of restoring the activity of a titanium-containing supported catalyst which has been used to catalyze an oxidation reaction such as the epoxidation of an olefin with an organic hydroperoxide. Regeneration is accomplished by contacting the spent heterogeneous catalyst with one or more specific types of solvents, preferably at a moderately elevated temperature.

BACKGROUND OF THE INVENTION

U.S. Pat. No. 4,367,342 discloses an olefin epoxidation process wherein an olefin is contacted with an organic hydroperoxide in the presence of an insoluble catalyst comprised of an inorganic oxygen compound of titanium. The patent discloses that at the conclusion of the reaction, the resulting product mixture may be separated and the products recovered by conventional methods such as fractional distillation, selective extraction, filtration and the like. The patent further teaches that the catalyst may be recycled for further utilization. Unfortunately, heterogeneous catalysts of the type disclosed in U.S. Pat. No. 4,367,342, for reasons which are not fully understood, tend to slowly deteriorate in performance when used repeatedly or in a continuous process for a prolonged period of time. In particular, the activity of the catalyst (as measured by the amount of olefin or organic hydroperoxide converted per pass or in a given period of time) decreases with time to a point where continued use of the catalyst charge no longer becomes economically viable. Due to the relatively high cost of synthesizing this type of catalyst, regeneration of the used catalyst would be greatly preferred over replacement.

It has previously been proposed that satisfactory regeneration might be achieved by blowing with hot air to burn away the impurities on the catalyst. However, heating the used catalyst at temperatures typically utilized for regeneration of other heterogeneous catalysts (e.g., zeolites), even for prolonged periods of time, fails to sufficiently improve the activity of the titanium-containing catalysts described hereinabove. Moreover, catalytic activity is not completely restored by heating at 500° C., even though substantially all organic impurities in the catalyst are removed at such temperatures. Although we have found that significantly higher temperatures are effective for reactivation purposes, a regeneration process which operates at such elevated temperatures is not ideal due to the increased utility and construction costs associated therewith. Thus, it would be desirable to develop alternative regeneration methods capable of operating at lower temperatures such that regeneration could be easily performed in situ, i.e., the same vessel in which the epoxidation is carried out.

SUMMARY OF THE INVENTION

The invention provides a method of regenerating a used non-zeolitic heterogeneous catalyst composition comprised of an inorganic oxygen compound of silicon in chemical combination with an inorganic oxygen compound of titanium. Said method comprises contacting the used non-zeolitic heterogeneous catalyst composition with a solvent selected from the group consisting of water, alcohols, ketones, ethers, nitriles, esters, aromatic hydrocarbons, and mixtures thereof to produce a reactivated heterogeneous catalyst composition.

DETAILED DESCRIPTION OF THE INVENTION

The catalysts regenerable by practice of the present invention are characterized as heterogeneous, that is, essentially insoluble in an oxidation reaction mixture, and non-zeolitic. Such catalyst compositions comprise an inorganic oxygen compound of silicon in chemical combination with an inorganic oxygen compound of titanium (e.g., an oxide or hydroxide of titanium). The inorganic oxygen compound of titanium is preferably combined with the oxygen compound of silicon in a high positive oxidation state, e.g., as tetravalent titanium. The proportion of the inorganic oxygen compound of titanium contained in the catalyst composition can be varied, but generally the catalyst composition contains, based on total catalyst composition, at least 0.1% by weight of titanium with amounts from about 0.2% by weight to about 50% by weight being preferred and amounts from about 0.2% to about 10% by weight being most preferred.

Catalysts of this type are well-known in the art and are described, for example, in U.S. Pat. Nos. 4,367,342, 4,021,454, 3,829,392 and 3,923,843, European Patent Publication Nos. 0129814, 0345856, 0492697 and 0734764, Japanese Kokai No. 77-07,908 (Chem. Abstracts 87:135000s), PCT Application No. WO 94/23834, German Patent Document No. 3,205,648, and Castillo et al., *J. Catalysis* 161, pp. 524–529 (1996), the teachings of which are incorporated herein by reference in their entirety.

The oxygen compound of silicon is an inorganic siliceous solid containing a major proportion of silica. Amorphous (i.e., non-crystalline) silicon compounds are particularly preferred for use. In general, suitable inorganic siliceous solids are further characterized by having a relatively large surface area in relation to their mass. The term used herein and one normally used in the art to express the relationship of surface area to mass is "specific surface area". Numerically, specific surface area will be expressed as square meters per gram ($m^2/g$). Generally, the inorganic siliceous solid has a specific surface area of at least 1 $m^2/g$ and preferably the average specific surface area is from 25 $m^2/g$ to 800 $m^2/g$.

Suitable inorganic siliceous solids include synthetic porous silicas consisting of particles of amorphous silica flocculated or linked together so that they form relatively dense, close-packed masses. Representatives of such materials are silica gel and precipitated silica. These silica products are porous, in that they have numerous pores, voids, or interstices throughout their structures.

Other suitable inorganic siliceous solids include synthetic silica powders consisting of particles of amorphous silica flocculated in open-packed, readily disintegrated, loosely knit aggregates. Illustrative silica powders include fumed, pyrogenic silicas obtained by the combustion of hydrogen and oxygen with silicon tetrachloride or tetrafluoride.

Synthetic inorganic oxide materials containing a major proportion of silica comprise another class of inorganic siliceous solids. Such materials are known as refractory oxides and include silica-alumina, silica-magnesia, silica-zirconia, silica-alumina-boric and silica-alumina-magnesia.

Particularly preferred synthetic inorganic siliceous solids are those consisting essentially of pure silica, e.g., materials containing at least 90% silica.

The preparation of the catalyst may be accomplished by a variety of techniques known in the art. One such method involves impregnating an inorganic siliceous solid support with a titanium tetrahalide (e.g., $TiCl_4$) either by solution or vapor phase impregnation, followed by drying and then calcination at an elevated temperature (e.g., 500° C. to 900° C.). Vapor phase impregnation is described in detail in European Patent Pub. No. 0345856 (incorporated herein by reference in its entirety). In another technique, the catalyst composition is suitably prepared by calcining a mixture of inorganic siliceous solids and titanium dioxide at an elevated temperature, e.g., 500° C. to 1000° C. Alternatively, the catalyst composition is prepared by cogelling a mixture of a titanium salt and a silica sol by conventional methods of preparing metal supported catalyst compositions. In still another technique, the catalyst composition is prepared by the surface reaction of silanol groups of an inorganic siliceous solid with a titanium salt by the procedure disclosed in U.S. Pat. No. 3,166,542 of Orzechowski and McKenzie, issued Jan. 19, 1965, U.S. Pat. No. 3,220,959 of Orzechowski, issued Nov. 30, 1965 or U.S. Pat. No. 3,274,120 of Aftandilian, issued Sep. 20, 1966. The catalyst composition is also suitably prepared by the reaction of hydroxyl groups of titanium dioxide containing such groups with a silicon tetrahalide using the same surface reaction procedure disclosed in the above patents. In yet another technique, a catalyst composition comprising a fumed, pyrogenic titania-silica is prepared by the combustion of hydrogen and oxygen with a mixture of silicon tetrahalide and titanium halide in accordance with conventional methods of preparing finely-divided fumed metal oxides and silica. An alternative method involves grafting various amounts of titania over the hydroxylated surface of an inorganic siliceous solid using a titanium tetraalkoxide. Other techniques for incorporating an oxide or hydroxide of titanium on an inorganic siliceous-solid such as dry-mixing, co-precipitation, impregnation and ion-exchange are also suitably employed.

One class of heterogeneous catalysts particularly suitable for reactivation using the methods described herein is titania-on-silica (also sometimes referred to as "$TiO_2/SiO_2$"), which comprises titania (titanium dioxide) supported on silica (silicon dioxide). The titania-on-silica may be in either silylated or nonsilylated form.

The catalyst composition is optionally, and preferably, subject to a pretreatment or activation prior to utilization in an oxidation process. The precise method of pretreatment will depend in part upon the form of chemical combination in which the components are provided, but in general the pretreatment comprises heating an initially prepared catalyst in an atmosphere of a non-reducing gas such as nitrogen, argon, carbon monoxide or, preferably, an oxygen-containing gas, e.g., air. One function served by this type of pretreatment operation is to convert the catalyst components into the form of inorganic oxygen compounds if these components are not initially provided in these forms. For example, residual halide or alkoxy groups attached to silica or titanium atoms may be replaced by oxygen or hydroxy groups. Temperatures from about 350° to about 800° C. are generally satisfactory for such purpose. Typical pretreatment times are from about 1 to 18 hours. Subsequent to pretreatment, the titanium catalyst is employed in any convenient physical form, for example, as powder, flakes, spheres or pellets.

Any titanium-halide bonds remaining after calcination may be hydrolyzed. Hydrolysis may be effected with steam at an elevated temperature, preferably in the range of from 150° C. to 400° C.

Another pretreatment method which may be utilized is to treat the catalyst with an organic silylating agent at elevated temperature. Such methods are well-known in the art and are described for example, in U.S. Pat. Nos. 3,829,392 and 3,923,843 (incorporated hereby by reference in their entirety). Suitable silylating agents include organosilanes, organosilylamines and organosilazanes. Silylation is typically performed after heating the catalyst at an elevated temperature (e.g., after calcination).

The aforedescribed heterogeneous catalyst compositions are typically utilized in oxidation reactions and are particularly useful for catalyzing the epoxidation of olefins using organic hydroperoxides. Olefin epoxidations of this type are well-known in the art and are described, for example, in U.S. Pat. No. 4,367,342 (incorporated herein by reference in its entirety).

As the olefin reactant in this process may be employed any organic compound having at least one aliphatic olefinically unsaturated carbon-carbon double bond, generally containing from 2 to 30 carbon atoms, but preferably from 3 to 10 carbon atoms. Especially for use are linear alpha olefins of 3 to 10 carbon atoms such as propylene, 1-butene, 1-pentene, 1-octene, and 1-decene.

The hydrocarbon used to prepare the organic hydroperoxide should contain at least one secondary or tertiary carbon atom (i.e., a tetra-substituted carbon atom wherein one or two of the substituents are hydrogen atoms and the remaining substituents are hydrocarbyl groups). Preferred hydrocarbons include $C_4$–$C_{20}$ aliphatic hydrocarbons, $C_7$–$C_{20}$ aralkyl hydrocarbons and mixtures thereof. Specific illustrative hydrocarbons include isobutane, ethyl benzene, cyclohexane, isopentane, 2-methyl pentane, methyl cyclohexane, tetrahydronaphthalene, cumene, diethyl benzene, 3-methyl pentane, and the like.

The organic hydroperoxide reactants used are secondary or tertiary hydroperoxides, including alkyl hydroperoxides and aralkyl hydroperoxides, wherein a hydroperoxy group is substituted for a hydrogen atom in the starting hydrocarbon. Suitable organic hydroperoxides thus include tertiary butyl hydroperoxide, tertiary amyl hydroperoxide, tertiary hexyl hydroperoxide, tertiary octyl hydroperoxide, ethyl benzene hydroperoxide, tetralin hydroperoxide, cumene hydroperoxide, cyclohexyl hydroperoxide, methyl cyclohexyl hydroperoxide, alpha-ethyl benzyl hydroperoxide, alpha-alpha diethyl benzyl hydroperoxide, and diisopropylene benzene hydroperoxide.

In the epoxidation reaction, the molar ratio of olefin reactant to hydroperoxide can vary over a wide range and a molar excess of either the olefin reactant or hydroperoxide of up to as high as 100:1 can be used. In general, molar ratios of olefin reactant to hydroperoxide varying from about 50:1 to about 1:10 are satisfactory, although it is preferred to employ molar ratios of olefin reactant to hydroperoxide of about 20:1 to about 1:1.

The organic hydroperoxide may be supplied in dilute or concentrated form, with the organic hydroperoxide generally being present in the crude oxidation product and the purified oxidation product at a concentration of about 5 to 70 percent by weight. The crude oxidation product is prepared by direct oxidation methods, such methods being well-known in the art. For example, molecular oxygen may be passed through the hydrocarbon to convert a portion of the hydrocarbon to the corresponding organic hydroperoxide. Such processes are described, for example, in U.S. Pat. Nos. 2,845,461, 3,351,635, 3,459,810, 3,475,498, 2,867,666, 3,351,635, 3,459,810, 3,475,498 and 4,966,706, all of which are incorporated herein by reference in their entirety.

Typically, the hydrocarbon oxidation is carried out in the absence of catalyst at a temperature of about 100° C. to 200° C. and 10 to 500 psia for an amount of time sufficient to achieve the desired degree of conversion. Either pure oxygen, air, or oxygen combined with an inert gas such as nitrogen can be used. Preferably, the hydrocarbon conversion is in the range of 1 to 50%, with the range of 5 to 20% being preferred where the hydrocarbon is ethylbenzene.

The epoxidation is conducted in the liquid phase in solvents or diluents which are liquid at reaction temperature and pressure and are substantially inert to the reactants and the products produced therefrom. Particularly preferred solvents are the hydrocarbons employed for producing the organic hydroperoxide reactants, e.g., alkylbenzenes such as ethylbenzene and isopropylbenzene and tertiary alkanes (an alkane containing a carbon atom attached to a hydrogen atom and 3 other carbon atoms) such as isobutane and isohexane. In certain modifications of the epoxidation process, a portion of the olefin reactant serves as the reaction solvent and no added solvent is needed. In most instances, however, added solvent is used. Amounts up to about 20 moles of solvent per mole of organic hydroperoxide are satisfactory. The process is preferably conducted in an inert reaction environment so that the present of reactive materials such as water is desirably avoided. Suitable reaction conditions are therefore substantially anhydrous.

The epoxidation reaction is suitably conducted by any of a variety of procedures. In one modification, the entire amounts of reactants, the catalyst and the solvent are charged to an autoclave or similar pressure reactor and the reaction mixture is maintained with agitation at reaction temperature and pressure for the desired reaction period. In another modification, one reactant is added to the remaining reaction mixture components in increments, as by adding the organic hydroperoxide to a mixture of the olefin reactant, the catalyst and the solvent maintained at the selected reaction temperature and pressure. In yet another modification, reaction is effected in a continuous manner as by contacting the olefin reactant, the hydroperoxide and the solvent during passage through a reaction zone in which the solid catalyst is maintained in particulate form either as a slurry, moving bed, fluidized bed or fixed bed, for example. The liquid containing the reactants may be passed through the catalyst bed, so that the effluent from the reaction zone is essentially free from catalyst. By any modification, the epoxidation process is conducted at moderate temperatures and pressures. Suitable reaction temperatures vary from about 25° C. to about 200° C., but preferably from 50° C. to 150° C. The reaction is preferably conducted at or above atmospheric pressure. The precise pressure is not critical so long as the reaction mixture is maintained substantially in a non-gaseous phase. Typical pressures vary from about 1 atmosphere to about 100 atmospheres. The epoxidation may successfully be carried out in a batch-wise, continuous, or semi-continuous manner.

The spent catalyst may be separated in solid form from any liquid components of the reaction mixture prior to regeneration. It is not, however, necessary to completely dry the recovered catalyst prior to regeneration since any minor amounts of epoxidation reaction solvent, reactants, and the like adsorbed on the catalyst can be readily removed and disposed of during such regeneration. Where the catalyst has been deployed in the form of a slurry, it may be readily collected by filtration, centrifugation, decantation, or other such mechanical means and then transferred into a vessel which is suitable for carrying out the regeneration. Alternatively, where the catalyst has been used as a fixed bed, the liquid components may be simply drained or pumped away from the spent catalyst and regeneration conducted in the same vessel as the catalytic epoxidation process. In a fixed bed embodiment of the invention, it is preferred to pass the regeneration solvent through the catalyst as a flowing stream such that impurities washed from the catalyst are continually carried away from the fixed bed. Liquid hourly space velocities in the range of from 0.1 to 24 are generally satisfactory. When the epoxidation reaction is carried out in a fixed bed or a continuously agitated bath, the spent catalyst may be washed with the regeneration solvent by supplying the solvent instead of the epoxidation reaction raw materials to the reactor. When the epoxidation reaction is performed as a batch-type reaction, the catalyst may be solvent washed by removing the supernatant solution following epoxidation, introducing the regeneration solvent to the reactor, agitating the solvent (preferably, while heating at a moderately elevated temperature), and again removing the supernatant solution.

Suitable solvents for practice of the regeneration process are selected from water, alcohols, ketones, ethers, nitriles, esters, aromatic hydrocarbons, and mixtures thereof. Surprisingly, it has been found that other types of solvents are considerably less effective in restoring catalytic performance. The use of water is particularly desirable, not only because it tends to quickly reactivate the spent catalyst, but also because of its low cost, non-flammability and ease of disposal. Methanol has also been found to be particularly effective in restoring catalyst activity. Preferred alcohols include $C_1$–$C_{10}$ aliphatic alcohols as well as $C_7$–$C_{12}$ aralkyl alcohols. Illustrative $C_1$–$C_{10}$ aliphatic alcohols include straight chain, branched and cyclic mono- alcohols such as methanol, ethanol, n-propyl alcohol, isopropyl alcohol, n-butanol, sec-butanol, iso-butanol, t-butyl alcohol, cyclohexanol, 2-ethyl hexyl alcohol, and the like. Suitable $C_1$–$C_{10}$ aliphatic alcohols also include diols and oligomers and mono-ethers thereof such as ethylene glycol, diethylene glycol, propylene glycol, tripropylene glycol, propylene glycol mono-methyl ether, 1,4-butanediol, neopentyl glycol, 1,3-propanediol, 2-methyl-1,3-propanediol, and the like. Examples of $C_7$–$C_{12}$ aralkyl alcohols include those alcohols wherein an alkyl group is substituted with both a hydroxy group and an aromatic group such as, for example, benzyl alcohol, alpha-methyl benzyl alcohol, alpha-ethyl benzyl alcohol, dimethyl benzyl alcohol, and the like. Ketones containing from 3 to 10 carbon atoms may also be utilized including, for example, acetone, acetophenone, 2-butanone, and cyclohexanone. Suitable ethers include, but are not limited to, straight chain, branched and cyclic aliphatic ethers, with $C_2$–$C_8$ aliphatic ethers such as diethyl ether and tetrahydrofuran being preferred. Aliphatic nitriles containing from two to ten carbon atoms such as acetonitrile may also be used. Preferred esters include $C_3$–$C_{10}$ aliphatic esters (both acyclic and cyclic) such as methyl acetate, ethyl acetate, gamma-butyrolactone, and the like. Aromatic hydrocarbons may be unsubstituted or substituted with alkyl groups or the like; particularly preferred aromatic hydrocarbons include $C_6$–$C_{12}$ compounds such as benzene, toluene, ethyl benzene, xylene, cumene, n-propyl benzene, and the like.

Without wishing to be bound by theory, it is believed that compounds which are relatively small in size are generally more effective in restoring catalyst activity because they may readily enter the pores of the catalyst. However, size alone is not a good predictor of effectiveness in view of the fact that washing with propylene or N-methyl pyrrolidone has little effect on catalyst performance.

The solvent is contacted with the used heterogeneous catalyst composition for a time and at a temperature effective to improve the activity of the composition (as measured by the rate at which an olefin and an organic hydroperoxide react to form epoxide). It is particularly effective to perform such contacting at a temperature at or above room temperature but less than the decomposition temperature of the solvent selected for use. While temperatures up to 400° C. are generally useful, operation within the range of from 50° C. to 250° C. is typically sufficient to improve catalytic performance within a reasonable period of time (e.g., 0.5 to 12 hours). The pressure and temperature can be selected to provide supercritical conditions. Pressures of from 0 to 1000 psig are generally useful for purposes of this invention. Preferably, the pressure is sufficient to maintain the washing solvent substantially as a liquid phase.

In a particularly preferred embodiment of the invention, the used heterogeneous catalyst composition is contacted with a $C_1$–$C_5$ aliphatic alcohol (either alone or admixed with another solvent such as water) at a temperature of from 100° C. to 175° C. at a pressure sufficient to maintain the solvent substantially in the liquid phase.

Following solvent treatment, the regenerated catalyst may be further treated if so desired prior to reuse in an oxidation reaction to further modify its catalytic properties. For example, the washed catalyst may be calcined by heating to an elevated temperature (e.g., 400° C. to 900° C.) in the presence of oxygen. A particularly desirable additional treatment involves reacting the reactivated catalyst with a silylating agent. Illustrative silylating agents include organosilanes, organosilylamines, and organosilazanes. Organosilanes containing from one to three organic substituents may be utilized, including, for example, chlorotrimethylsilane, dichlorodimethylsilane, nitrotrimethylsilane, chlorotriethylsilane, chlorodimethylphenylsilane and the like. Also suitable for use are the hexaalkyl substituted disilazanes such as, for example, hexamethyldisilazane. The techniques described in U.S. Pat. Nos. 3,829,392 and 3,923,843 (incorporated herein by reference in their entirety) for silylation of freshly prepared titanium containing supported catalysts may be adapted for such purpose. Silylation of the washed catalyst may be performed either before or after the optional calcination step.

The solvent-treated catalyst, prior to silylation, may be subjected to hydration wherein the catalyst is contacted with water and then heated or first heated and then contacted with water vapor. Suitable hydration temperatures are typically at least 100° C. and preferably in the 150° C. to 450° C. range with such heating being continued for 0.5 to 10 hours. This hydration step is not essential, however.

Treatment with the silylating agent may be performed either in the liquid phase (i.e., where the silylating agent is applied to the catalyst as a liquid, either by itself or as a solution in a suitable solvent such as a hydrocarbon or even the solvent used to treat the catalyst, provided said solvent does not react with or decompose the silylating agent) or in the vapor phase (i.e., where the silylating agent is contacted with the catalyst in the form of a gas). Treatment temperatures are preferably in the 100° C. to 450° C. range, with somewhat higher temperatures (e.g., 300° C. to 425° C.) being generally preferred wherein the silylating agent is an organohalosilane and somewhat lower temperatures (e.g., 100° C. to 300° C.) being preferred for the organosilazanes.

The regenerated catalyst which has been reactivated in accordance with the process of the invention may be admixed with freshly prepared catalyst prior to reuse, if so desired, or used directly. In one embodiment of the invention, the treatment solvent is selected so as not to interfere with epoxidation when the regenerated catalyst is reused. For example, where epoxidation is performed in the presence of ethylbenzene solvent, ethylbenzene is desirably used as the treatment solvent so that drying of the reactivated catalyst is not necessary. In other embodiments where the presence of large amounts of the treatment solvent may adversely affect the epoxidation results, the reactivated catalyst is first dried to reduce the level of residual treatment solvent to an acceptable level.

EXAMPLES

Example 1

A non-silylated titania-on-silica catalyst was prepared in accordance with the procedures described in U.S. Pat. No. 3,923,843 and used to catalyze the epoxidation of propylene with ethyl benzene hydroperoxide in a fixed bed reactor for 526 hours. After removal from the reactor, the used catalyst gave only 23% conversion and 90% selectivity to epoxide in a batch epoxidation of 1-octene with ethylbenzene hydroperoxide (1 hour, 90° C.). Drying in a 120° C. vacuum oven had little effect on the activity of the catalyst (27% conversion, 100% epoxide selectivity).

Portions of the dried deactivated catalyst were washed with various solvents for two hours at the temperatures shown in the following table. The washed catalyst portions were subsequently dried in a 120° C. vacuum oven to remove residual solvent, then tested in batch 1-octene epoxidation using ethyl benzene hydroperoxide (one hour, 90° C.).

| Wash Solvent | Wash Temperature ° C. | % EBHP Conversion | % Epoxide Selectivity |
|---|---|---|---|
| N-methylpyrrolidone* | 100 | 21 | 93 |
| propylene glycol | 100 | 39 | 85 |
| ethyl benzene | 100 | 42 | 86 |
| alpha-methyl benzyl alcohol | 100 | 62 | 86 |
| isopropanol | 80 | 49 | 87 |
| gamma butyrolactone | 100 | 24 | 94 |
| tetrahydrofuran | 60 | 44 | 84 |
| deionized water | 80 | 66 | 86 |

*comparative example

The epoxidation results confirmed that water, alcohols, aromatic hydrocarbons, and ethers more effectively improved catalyst performance than the other solvents tested.

Example 2

Example 1 was repeated, but using a silylated titania-on-silica catalyst prepared in accordance with the procedures described in U.S. Pat. No. 3,923,843. The following results were observed:

| Solvent | Wash Temperature ° C. | % EBHP Conversion |
|---|---|---|
| none (120° vacuum oven) | — | 11 |
| N-methylpyrrolidone* | 100 | 14 |
| propylene glycol | 100 | 12 |
| ethyl benzene | 100 | 14 |
| alpha-methyl benzyl alcohol | 100 | 18 |
| isopropanol | 80 | 10 |
| gamma butyrolactone | 100 | 11 |
| tetrahydrofuran | 60 | 9 |
| deionized water | 80 | 33 |

*comparative example

Under the aforedescribed regeneration and epoxidation conditions, water and alpha-methyl benzyl alcohol found to be the most effective solvents for restoring the activity of the catalyst. For reasons which are not well understood, the other treatment solvents evaluated were approximately equally ineffective for such purpose. The observed selectivity to epoxide was substantially independent of the solvent employed and in each case was approximately equivalent to that of the deactivated catalyst.

Example 3

A deactivated catalyst was prepared by contacting a titania-on-silica catalyst prepared in accordance with the procedures described in U.S. Pat. No. 3,923,843 at 100° C. with an ethyl benzene solution of a distillation bottoms fraction recovered from a propylene oxide/styrene plant. Catalyst deactivated in this manner has been found to be similar in performance to catalyst deactivated by actual prolonged use in an olefin epoxidation reaction.

Samples of the deactivated titania-on-silica catalyst were washed with various solvents in a fixed bed at 100° C. and 150 psig. The epoxidation results observed for freshly prepared catalyst, deactivated catalyst and the treated catalysts are shown in the following table:

| Wash Solvent | % Na Removed | % EBHP Conversion | % Epoxide Selectivity |
|---|---|---|---|
| fresh catalyst | — | 75 | 83 |
| deactivated catalyst | — | 50 | 85 |
| water | 29 | 53 | 84 |
| acetone | 11 | 53 | 87 |
| isopropanol | 31 | 59 | 85 |

Example 4

Samples of a deactivated silylated titania-on-silica catalyst were introduced into a fixed bed reactor and washed with different solvents under the conditions indicated in the following table:

| Catalyst | Wash Solvent | Bed Volumes of Solvent | Wash Temp. ° C. | Pressure, psia | EBHP Conversion, % | Epoxide Selectivity % | Activity Recovered % |
|---|---|---|---|---|---|---|---|
| Fresh | — | — | — | — | 70 | 86 | — |
| Deactivated | none | — | — | — | 16 | 80 | — |
| Deactivated/Washed | ethyl benzene | 72 | 140 | 150 | 18 | 77 | 2 |
| Deactivated/Washed | water | 72 | 140 | 150 | 13 | 77 | (3) |
| Deactivated/Washed | isopropanol | 72 | 140 | 150 | 26 | 88 | 12 |
| Deactivated/Washed | methanol | 72 | 110 | 150 | 59 | 84 | 70 |

The washed catalysts were evaluated as catalysts for the batch epoxidation of 1-octene under the following conditions: 90° C., 1 hour, 6:1 1-octene:ethyl benzene hydroperoxide (EBHP). The percent activity recovered is calculated as a percentage of the rate k of the freshly prepared catalyst. It was found that, under the treatment conditions employed, methanol was significantly more effective in restoring the activity of the deactivated catalysts than the other solvents tested.

Example 5

The efficacy of various aliphatic alcohols in restoring the performance of a deactivated titanium-on-silica catalyst was determined using the same procedures described in Example 5. The reactivation conditions used and epoxidation results obtained are shown in the following table:

| Catalyst | Wash Solvent | Bed Volumes of Solvent | Wash Temp., ° C. | Pressure psia | EBHP Conversion % | Epoxide Selectivity % | Activity Recovered % |
|---|---|---|---|---|---|---|---|
| Fresh | — | — | — | — | 67 | 85 | — |
| Deactivated | — | — | — | — | 25 | 82 | — |
| Deactivated/Washed | methanol | 72 | 110 | 150 | 60 | 84 | 76 |
| Deactivated/Washed | ethanol | 72 | 110 | 150 | 41 | 85 | 29 |
| Deactivated/Washed | n-propanol | 72 | 140 | 150 | 47 | 87 | 42 |
| Deactivated/Washed | isopropanol | 72 | 140 | 150 | 14 | 92 | <0 |
| Deactivated/Washed | t-butanol | 72 | 140 | 150 | 38 | 86 | 23 |

Significant improvement in catalytic activity was observed for each of the solvents tested, except in the example where isopropanol was utilized. It is not known why a decrease in activity as compare to the deactivated catalyst was observed under these conditions using isopropanol, particularly since in other tests such as those described in Examples 1–4 isopropanol was found to be an effective regeneration solvent.

Example 6

This example demonstrates the effect of increasing temperature and pressure when methanol is employed as the washing solvent. A deactivated titania-on-silica catalyst was washed with methanol under the conditions shown in the following and then evaluated as an epoxidation catalyst.

| Catalyst | Wash Solvent | Bed Volumes of Solvent | Temp., °C. | Pressure psi | EBHP Conversion % | Epoxide Selectivity % | Activity Recovered, % |
|---|---|---|---|---|---|---|---|
| Fresh | — | — | — | — | 67 | 86 | — |
| Deactivated | — | — | — | — | 22 | 80 | — |
| Deactivated/ Washed | methanol | 24 | 135 | 800 | 64 | 86 | 90 |

The activity of the deactivated catalyst was restored to nearly that of freshly prepared catalyst by practice of the regeneration process claimed herein.

Example 7

Samples of a deactivated catalyst prepared in accordance with the procedures described in Example 3 were washed with various solvents in a fixed bed under the conditions shown in the following table.

| Wash Solvent | Solvent Amt. (bed volumes) | Wash Temp. °C. | Wash Pressure psig | % EBHP Conversion | % Epoxide Selectivity | % Activity Recovered |
|---|---|---|---|---|---|---|
| fresh catalyst | — | — | — | 65 | 85 | — |
| deactivated catalyst | — | — | — | 13 | 80 | — |
| acetonitrile | 72 | 110 | 150 | 25 | 84 | 16 |
| ethyl acetate | 66 | 110 | 150 | 24 | 83 | 15 |
| acetone | 72 | 80 | 150 | 17 | 78 | 5 |
| tetrahydrofuran | 72 | 110 | 150 | 22 | 83 | 12 |
| diethyl ether | 72 | 90 | 150 | 17 | 79 | 5 |
| N-methyl pyrrolidone* | 72 | 110 | 150 | 11 | 65 | <0 |
| gamma butyrolactone | 72 | 110 | 150 | 26 | 83 | 18 |

*comparative example

The washed catalysts were tested in batch 1-octene epoxidation (6:1 octene:EBHP) at 90° C. (1 hour). Improvement in catalytic activity was observed for each solvent evaluated except for N-methylpyrrolidone.

We claim:

1. A method of regenerating a used non-zeolitic heterogeneous catalyst composition comprised of an oxygen compound of silicon in chemical combination with an inorganic oxygen compound of titanium and which has been used to catalyze epoxidation of an olefin using an organic hydroperoxide, said method comprising contacting said used heterogenous catalyst composition with a solvent selected from the group consisting of water, alcohols, ketones, ethers, esters, nitriles, aromatic hydrocarbons, and mixtures thereof in the absence of the olefin and the organic hydroperoxide at a temperature of 20° C. to 400° C. to produce a reactivated heterogeneous catalyst composition.

2. The method of claim 1 wherein the solvent is selected from the group consisting of water, $C_1$–$C_{10}$ aliphatic alcohols, $C_7$–$C_{12}$ aralkyl alcohols, $C_3$–$C_{10}$ ketones, $C_2$–$C_8$ aliphatic ethers, $C_2$–$C_{10}$ aliphatic nitrites, $C_3$–$C_{10}$ aliphatic esters, $C_6$–$C_{12}$ aromatic hydrocarbons, and mixtures thereof.

3. The method of claim 1 wherein the temperature is from 50° C. to 250° C.

4. The method of claim 1 wherein the oxygen compound of silicon is silica.

5. The method of claim 1 comprising the additional step of calcining the reactivated heterogeneous catalyst composition.

6. The method of claim 1 comprising the additional step of silylating the reactivated heterogeneous catalyst composition with an organic silylating agent.

7. The method of claim 1 wherein the organic oxygen compound of titanium is selected from the group consisting of titanium oxides, titanium hydroxides, and mixtures thereof.

8. The method of claim 1 wherein the used heterogeneous catalyst composition is maintained in a fixed bed and the solvent passed through the fixed bed.

9. The method of claim 1 wherein said contacting is performed for a period of time of from 0.5 hours to 12 hours.

10. A method of regenerating a used non-zeolitic heterogeneous catalyst composition which has been used to catalyze epoxidation of an olefin with an organic hydroperoxide and which is method comprised of silica in chemical combination with an inorganic oxygen compound of titanium, said method comprising contacting said used heterogenous catalyst composition with a solvent selected from the group consisting of $C_1$–$C_{10}$ aliphatic alcohols, $C_7$–$C_{12}$ aralkyl alcohols, $C_3$–$C_{10}$ ketones, $C_2$–$C_8$ aliphatic ethers, $C_2$–$C_{10}$ aliphatic nitrites, $C_3$–$C_{10}$ aliphatic esters, $C_6$–$C_{12}$ aromatic hydrocarbons, and mixtures thereof in the absence of the olefin and the organic hydroperoxide at a temperature of from 50° C. to 250° C. for a period of time of from 0.5 hours to 12 hours to produce a reactivated non-zeolitic heterogeneous catalyst composition.

11. The method of claim 10 wherein the solvent is selected from the group consisting of water, methanol, ethanol, n-propanol, isopropanol, n-butanol, iso-butanol, sec-butanol, t-butanol and mixtures thereof.

12. The method of claim 10 comprising the additional step of calcining the reactivated non-zeolitic heterogeneous catalyst composition.

13. The method of claim 10 comprising the additional step of silylating the reactivated non-zeolitic heterogeneous catalyst composition with an organic silylating agent.

14. The method of claim 1 wherein the inorganic oxygen compound of titanium is selected from the group consisting of titanium oxide, titanium hydroxides, and mixtures thereof.

15. The method of claim 10 wherein the used non-zeolitic heterogeneous catalyst composition is maintained in a fixed bed and the solvent passed through the fixed bed.

16. The method of claim 15 wherein the solvent is passed through the fixed bed at a liquid hourly space velocity of from 0.1 to 24.

17. The method of claim 10 wherein the used non-zeolitic heterogeneous catalyst composition is initially prepared by impregnating silica with titanium tetrachloride, drying, and calcining at a temperature of from 500° to 900° C.

18. A process comprising the steps of:
(a) contacting an olefin and an organic hydroperoxide with a non-zeolitic heterogeneous catalyst composition comprised of an oxygen compound of silicon in chemical combination with an inorganic oxygen compound of titanium by passing the olefin and the organic hydroperoxide through a reaction zone in which the non-zeolitic heterogeneous catalyst composition is maintained in particulate form at a temperature of from 50° C. to 150° C. to form an epoxide corresponding to the olefin; and
(b) contacting said non-zeolitic heterogeneous catalyst composition used in step (a) with a flowing stream consisting essentially of a solvent selected from the group consisting of water, alcohols, ketones, ethers, esters, nitriles, aromatic hydrocarbons and mixtures thereof at a temperature of 20° C. to 400° C. to reactivate the non-zeolitic heterogeneous catalyst composition.

19. The process of claim 18 wherein the non-zeolitic heterogeneous catalyst composition is in a fixed bed.

20. The process of claim 18 wherein the solvent is selected from the group consisting of water, $C_1$–$C_{10}$ aliphatic alcohols, $C_7$–$C_{12}$ aralkyl alcohols, $C_3$–$C_{10}$ ketones, $C_2$–$C_8$ aliphatic ethers, $C_2$–$C_{10}$ aliphatic nitriles, $C_3$–$C_{10}$ aliphatic esters, $C_6$–$C_{12}$ aromatic hydrocarbons, and mixtures thereof.

21. The process of claim 18 wherein the temperature is from 50° C. to 250° C.

22. The process of claim 18 wherein the oxygen compound of silicon is silica.

23. The process of claim 18 wherein the inorganic oxygen compound of titanium is selected from the group consisting of titanium oxides, titanium hydroxides, and mixtures thereof.

24. The process of claim 18 wherein said contacting in step (b) is performed for a period of time of from 0.5 hours to 12 hours.

25. The process of claim 18 wherein the non-zeolitic heterogenous catalyst composition is in a fixed bed and the flowing stream is passed through the fixed bed at a liquid hourly space velocity of from 0.1 to 24.

26. The process of claim 18 wherein the non-zeolitic heterogeneous catalyst composition is a titania-on-silica catalyst composition, the solvent is a $C_1$–$C_5$ aliphatic alcohol, and the temperature in step (b) is from 100° C. to 175° C.

* * * * *